United States Patent [19]

Mautone et al.

[11] Patent Number: 5,174,988
[45] Date of Patent: Dec. 29, 1992

[54] PHOSPHOLIPID DELIVERY SYSTEM

[75] Inventors: Alan J. Mautone, Morris Township, Morris County, N.J.; Joel Klayman, New Rochelle, N.Y.

[73] Assignee: Scientific Development & Research, Inc., Belleville, N.J.

[21] Appl. No.: 385,907

[22] Filed: Jul. 27, 1989

[51] Int. Cl.⁵ .................. A61K 9/12; A61K 9/127
[52] U.S. Cl. .................................. 424/45; 424/450
[58] Field of Search ............. 424/437, 45, 78, 450; 604/295

[56] References Cited

U.S. PATENT DOCUMENTS

| | | | |
|---|---|---|---|
| 4,370,349 | 1/1983 | Evans et al. | 424/365 |
| 4,394,722 | 7/1983 | Taylor | 424/85 |
| 4,505,935 | 3/1985 | Larsson | 514/779 |
| 4,508,703 | 4/1985 | Redziniak et al. | 424/38 |
| 4,731,210 | 3/1988 | Weder et al. | 424/450 |
| 4,814,161 | 5/1989 | Jinks et al. | 424/45 |
| 4,839,175 | 6/1989 | Guo et al. | 424/428 |
| 4,870,011 | 9/1989 | Suzuki et al. | 260/412.8 X |
| 4,883,658 | 11/1989 | Holly | 424/78 |
| 4,895,719 | 1/1990 | Radhakrishnan et al. | 424/45 |
| 4,923,700 | 5/1990 | Kaufman | 424/437 |
| 4,931,284 | 6/1990 | Exman et al. | 424/450 |
| 4,973,465 | 11/1990 | Baurain et al. | 424/406 |

Primary Examiner—Thurman K. Page
Attorney, Agent, or Firm—Frank Cozzarelli, Jr.

[57] ABSTRACT

A process to prepare lipid crystalline figures in fluorocarbon propellants for the delivery of therapeutically active substances which form amorphous films on delivery and which can be suspended in aqueous media to serve as a drug delivery system or, when used without therapeutically active substance, as an artificial tear.

5 Claims, No Drawings

PHOSPHOLIPID DELIVERY SYSTEM

FIELD OF INVENTION

This invention relates to a composition which is useful in the fields of (1) pharmaceutical or drug delivery, both by aerosolization into mammalian lungs, but is not limited to these organs in non-aqueous medium and by drops into the eyes in aqueous media and (2) artificial tears. A further aspect of this invention is directed to the process for preparing the delivery system, and the artificial tears.

DESCRIPTION

Background of Invention

The present invention has a wide range of usefulness in biomedicine. It serves as a vehicle for drug administration both into the lungs and into the eyes; in addition, the eye vehicle itself, without drugs, serves as artificial tears.

Two of the body's epithelial surfaces that are in direct contact with ambient air are the surfaces of the lung (airways and alveoli) and of the eyes (cornea-conjunctiva). Each of these surfaces is covered by an acellular essentially two-phase fluid system: the external phase, or layer, which interfaces with air, is lipidic and the internal phase or layer, which interfaces with tissue, is aqueous. A third layer possibly equivalent to the glycocalyx of other structures, is probably more closely bound to the epithelial surface.

Traditionally, pharmaceuticals, drugs and therapeutic materials have been administered to the body by various routes including topically, injection, inhalation, by mouth and into body cavities. Some problems result because the material circulates throughout the body possibly affecting other parts rather than the target area.

The Lungs

Research over the past 3 to 4 decades has revealed the composition and function of the acellular surface film of the lung, the so-called surfactant system. The system is a complex mixture of lipids, proteins and carbohydrates; as described in a recent review: Surfactants and the Lining of the Lung, The Johns Hopkins University Press, Baltimore, 1988. At the alveolar level its function is to prevent excessive accumulation of liquid within the alveolar airspace and to stabilize the alveoli and small-airways against collapse. These functions are achieved principally through the operation of phospholipids at the air/film interface. Whereas certain lung specific proteins of the system may influence this function (a highly speculative possibility, not yet defined), it is universally accepted that, unsaturated phospholipids, principally dipalmitoyl phosphatidyl choline (DPPC), impart to the surface its essential biophysical properties (liquid balance and stability) that sustain normal function. It is also clear that, whereas lipid composition differs somewhat between alveolar airspace and small airway airspace, the principal phospholipid at each surface is DPPC. DPPC is an amphoteric molecule that forms a monomolecular film at the air/lining interface with certain unique properties that explain its normal function: (1) the film, which spreads to cover all surfaces, achieves extremely low surface tension upon compression, e.g., during exhalation, thereby reducing the force that favors liquid movement into the airspace; (2) as airway or alveolar size falls, surface tension falls proportionately, thereby establishing a pressure equilibration among structures to prevent collapse; (3) because of its amphoteric structure, the film can form loose chemical associations with both hydrophobic and hydrophilic moieties and because of its high compressibility these associations can be broken upon film compression, thereby freeing the moiety from the interface. DPPC, which is the principal surfactant in all mammalian species examined to date, is synthesized by epithelial cells of the airspaces (the type 2 pneumocyte of the alveoli and an as yet unidentified cell of the airways) and secreted into the acellular lining layer as a variety of "myelin figures", i.e., lipid bilayers in a variety of structural conformations, including multilamellar, tubular myelin and conventional bilayer. It is generally agreed that the myelin figure conformation undergoes a process of unraveling at the air/lining interface, where the monomolecular film configuration is established. Implicit in this scheme of film formation are the concepts of "adsorption" of DPPC at the interface and "spreading" of DPPC at the surface. A second component of the surfactant system, cholesteryl palmitate (CP), appears to be an important adjuvant (Respir. Physiol. 38:235, 1979): Whereas, DPPC itself is adsorbed relatively slowly to the air/lining interface and, once adsorbate, spreads slowly, both these processes are accelerated significantly in the presence of relatively small amounts of CP. DPPC has been administered to infants with respiratory distress syndrome as a therapeutic measure to provide the afflicted infant with the substance, DPPC, in which he is deficient. Attempts have been made at replacement therapy by the use of aerosols, either with FREON propellant directly into a face mask from which the infant breathed, or with an aqueous aerosol generator into a chamber (incubator) in which the infant resided during the course of the disease. Later attempts at surfactant replacement therapy for respiratory distress syndrome include a variety of preparations that are administered (instilled) directly into the airways through an endotracheal tube. These preparations can be classified broadly as either "natural" or "artificial" surfactants. "Natural" surfactants, in general, contain all components of the surfactant system as isolated from human mitotic fluid or from animal lungs (principally bovine and porcine lungs). In these preparations, the isolated components of the surfactant system are suspended in aqueous medium which is then administered as bulk liquid injections into the infants' lungs. "Artificial" surfactants are generally preparations that utilize commercially available synthetic materials. Most preparations are delivered to the infant in bulk liquid suspensions (including liposomes and, in one case, in the form of lipoprotein) and; in another clinical trial a mixture of DPPC:Phosphatidylglycerol (PG) was blown into the lungs as dry powder. There have been varying degrees of success reported from the clinical trials of surfactant replacement therapy for treatment of respiratory distress syndrome. Most recently, a variety of phospholipid combinations, including saturated and unsaturated, neutral and polar phospholipids, have been employed in the process of liposome production. In contrast to the use of surfactant for therapeutic purposes (above), the liposomes have been formulated as vehicles to carry medications into the lungs. The liposome is essentially a lipid membrane-bound spherical vesicle, analogous to intracellular organelles, which encapsulates and stores in an aqueous phase the drug(s) to be delivered. Their probable mode of action is by adsorption or fusion to the cell surface, whence either the contents may be liberated and enter the cell by a number of transmembrane routes or the entire liposome may enter the cell by endocytosis. The lamellae that make up the lipid-crystals described herein provide enormous surfaces, e.g., conservatively estimated at 200 micrometers$^2$ for each 0.1 nanogram of phospholipid. Because of the amphoteric and lamellar nature of the crystals, they readily associate with both hydrophilic and hydrophobic molecules, an association that is maintained when these components are resuspended in an aerosol medium. When propelled from the metered-dose nebulizer, the fluorocarbon medium vaporizes rapidly and the DPPC:CP drug combination deposits on an aqueous surface, at 37° C., in the crystalline form, which then instantaneously spreads over the surface as an amorphous surface film carrying with it the therapeutic drug for which it serves as a vehicle. Studies in animals have shown quite definitively that the DPPC:CP vehicle is distributed on the lung surfaces uniformly (i.e., there is proportionate distribution to all regions of the lung as shown by radioisotope-tracking experimentally) and that it spreads rapidly leaving behind a surface film of essentially DPPC that is indistinguishable functionally from the normal surface. Indeed, it is known when lungs are depleted of DPPC experimentally, in the laboratory deposition of the DPPC:CP vehicle can reverse the functional abnormality (see Pediat. Res.,18:404A,1984. The vehicle system for the present invention can deliver, for example, 5.0 mg DPPC:CP (200:1 w/w), which if delivered quantitatively would cover 100% of the airspace surface in the lungs of normal adults. In fact, however, delivery is 10% to 85% efficient (depending on nozzle adapter used): Even at 10% efficiency, however, it is estimated that all conducting airway surfaces will receive medication. The amount aerosolized per actuation can be modified by varying the concentration of DPPC:CP in the fluorocarbon propellant or the size of the metering valve to yield 210 mg to 5.05 mg DPPC:CP per actuation. In this vehicle, the concentration of drugs can be varied over a wide range, depending on the drug's solubility characteristics. The ratio of DPPC:CP chosen (200:1; range to 20:1) has all the required surface characteristics that render it compatible with normal lung function and suitable as a vehicle for therapeutic drug administration. These advantages include (1) rapid adsorption to the air/liquid interface; (2) rapid spreading at the interface; (3) reduction of surface tension to near-zero; (4) versatile association with both hydrophobic and hydrophilic molecules; (5) delivery of these molecules over a wide surface area; (6) uniform delivery throughout the lung regions; and (7) delivery in sufficient quantity to reach all conducting airway surfaces.

The Eyes

The biophysical characteristics of the DPPC:CP drug delivery system that render it suitable for delivery via the pulmonary route also make it suitable for delivery in an ophthalmic aqueous medium.

The composition of the acellular film that covers cornea and conjunctiva (collectively "tear films") is not as well defined as it is for the lungs. The two layers of the tear film are the lipidic layer, secreted primarily by the Meibomian glands, and the underlying aqueous layer, secreted primarily by the accessory lacrimal glands. The lipidic layer, which interfaces with ambient air, serves a number of purposes: (1) It lubricates the juxtaposed conjunctival and corneal surfaces thereby facilitating lid movement (minimizing shear forces) and preventing lid to corneal adherence (anti-sticking). (2) It covers the aqueous layer and thereby minimizes evaporation (tear conservation). (3) With blinking its thickness varies, as conjunctival-corneal surface area changes, while it maintains a continuous film over the aqueous layer (rapid spreading following compression). (4) Following secretion, it spreads rapidly over the entire aqueous surface (rapid adsorption and spreading). (5) Surface tension at the lipid/aqueous interface is low (near-zero) so that fluid dynamics of the aqueous layer are not impeded by the lipidic layer (equilibrium of aqueous flux is practically independent of the lipid layer). (6) When aqueous equilibrium is disturbed (either positive or negative) the simultaneous changes in the local lipid film promote uniform re-distribution of the aqueous layer (geometric uniformity)). The lipid composition (Exptl. Eye Res. 15:515, 1973) is roughly sterol esters:wax esters:triglycerides:free fatty acids, 1.1:1:7.8:20.7 (w/w) and other, as yet unidentified lipids. Surface tension at the air/lipid interface is rather high, about 46.2 dynes/cm, and constant.

SUMMARY OF THE INVENTION

The present invention uniquely combines DPPC:CP in lipid-crystalline structures in fluorocarbon propellants in which therapeutically active agents, drugs or other materials can be carried into the lungs after actuation from a metered dose nebulizer. This composition upon addition of water can be used either without drugs as an artificial tear, or with drugs as a drug delivery system for the eye, but not limited to the eye. Other advantages will become apparent to those skilled in the art from the Detailed Description, Examples and Claims that follow.

According to the present invention, the above object is met by a process to prepare lipid crystalline figures in fluorocarbon propellants for the delivery of therapeutically active substances which form amorphous films on delivery and which can be suspended in aqueous media to serve as a drug delivery system or, when used without therapeutically active substance, as an artificial tear.

As used throughout the specification and claims, the phrase "therapeutically active" includes any substance which is capable of altering a body function, appearance or is a drug.

DETAILED DESCRIPTION OF THE INVENTION

The drug delivery system and artificial tears is comprised of a phospholipid, a neutral lipid, with a third component being the drug to be delivered and the fourth component being fluorocarbons when a propellent is needed. The major component is the phospholipid 1,2 dipalmitoyl phosphatidyl choline (DPPC), which is the most surface active of the phospholipids. DPPC can be synthesized. It is a phospholipid, a class of organic compounds that are the main constituents of cells and which are extractable by nonpolar solvents, i.e., chloroform, ether, acetone. The structural formula of DPPC is:

$$\begin{array}{c} \text{O} \\ \parallel \\ \text{CH}_3(\text{CH}_2)_{14}\text{C}-\text{O}-\text{CH}_2 \\ \text{CH}_3(\text{CH}_2)_{14}\text{C}-\text{O}-\text{CH} \quad \text{O} \\ \parallel \quad\quad\quad | \quad\quad | \\ \text{O} \quad\quad \text{H}_2\text{C}-\text{O}-\text{P}-\text{O}-\text{CH}_2\text{CH}_2\text{N}^+(\text{CH}_3)_3 \\ \parallel \\ \text{O} \end{array}$$

The phospholipid may be obtained commercially in a highly purified form from Fluka Chemical Co. of Ronkonkoma, N.Y. and Sigma Chemical Co. of St. Louis, Mo.

The DPPC is an essential component of both the drug delivery system and artificial tears, and is present in the composition over a fairly wide range. Percentages of DPPC may be as low as 90% and as high as 99.5% of the lipids by weight with essentially no change in in-vitro properties. However, 99.5% DPPC by weight is preferred.

The second component of the drug delivery system and artificial tears is cholesteryl palmitate (CP). This cholesterol ester is a neutral lipid which belongs to a class of organic compounds that are also cell constituents and are extractable by nonpolar solvents such as chloroform, methanol, ether, etc. The structural formula of CP is:

[Structural formula of cholesteryl palmitate]

CP may be obtained commercially in a highly purified form from Fluka Chemical Co and Sigma Chemical Co. The CP component constitutes a minor portion of the composition, since it is present in an amount ranging from 0.5% to 10% by weight of the composition. The preferred ratio of DPPC to CP is 99.5% DPPC to 0.5% CP by weight. However, the percentages may be altered as above without undue interference with desired properties which are essential for drug delivery and to achieve the desired zero surface tension. The mixture of 90 micrograms of albuterol, purchased from Schering Pharmeceuticals, Kenilworth, N.J. in 2 mg PC:CP/spray appears is the optimal combination.

The fluorocarbon propellants, namely trichlorodifluoromethane and dichlorodifluoromethane which are commercially available from Union Carbide Corp., Danbury, Conn. and Armstrong Laboratories West Roxbury, Mass., are essential for the formation of the lipid crystalline figures of the drug delivery systems and artificial tears. The fluorocarbon propellants are present over a range of 5 to 20 times, by weight, the amount of lipid, but the three components of DPPC, CP and fluorocarbon propellants are needed to obtain the required lipid crystalline figures.

The aqueous suspension of the drug delivery system and the artificial tears requires that the DPPC:CP in fluorocarbon propellants be solubilized in propylene glycol available from Union Carbide Corp. after the propellants have evaporated. Propylene glycol is a solubilizing agent commonly used in pharmaceutical manufacture. The hydrophobic nature of the DPPC and CP necessitates the use of propylene glycol so that the DPPC:CP crystal will be effectively suspended in the aqueous medium.

The final component of the drug delivery system is the particular drug to be delivered. The amphoteric nature of the major component, i.e., DPPC, makes it capable of carrying any drug or therapeutic agent. The composition of the aerosol drug delivery system uses the bronchodilator albuterol in the example preparation set forth below.

Example I

The aerosolized drug delivery system was prepared from chromatographically pure (greater than 99%) DPPC and CP. Both materials were purchased from suppliers on the commercial market where they are available from several chemical supply houses. Specifically, the DPPC and CP were purchased from Sigma Chem., St. Louis, Mo. All purchased materials were checked for purity by standard chromatographic analysis. The Albuterol-$SO_4$ can be purchased from Schering Pharmaceuticals or Glaxo Pharmaceuticals. The materials were then prepared in the fluorocarbon propellants which are also commercially available.

The DPPC and CP are mixed in the dry powder form in a weight ratio of 200:1 (DPPC:CP). To this is added Albuterol-$SO_4$ 200:1:0.09 by weight. Then 5 gms of this mixture are suspended in 55 gms of the first propellant, trichloromonofluromethane (P11) and subdivided into 30 ml Wheaton plastic-coated glass bottles with a 20 mm neck finish. Valois metering valves are crimped onto each bottle through which 40 gms of the second propellant, dichlorodifluoromethane (P12), was passed. The filled bottles are then gently shaken to disperse the solids, which are insoluble in the propellants. The bottles are immersed in a water-bath to test for leaks, and then fitted with a Valois oral inhalation adapter. The suspension is homogeneous. After standing at room temperature for about three days, a pellicle forms on top of the propellants but is easily resuspended by gentle shaking. The size of the metering valve can be varied to deliver from 1 mg up to 5.4 mg of the DPPC:CP:albuterol mixture. Purity of the components was retained, microbe-free, for at least one year after manufacture.

The composition of the artificial tears and the drug delivery system for the eyes is identical except for the addition of drug. The artificial tears will be set forth in Example II and the drug delivery system for the eyes will be set forth in Example III.

Example II

Chromatographically pure DPPC and CP (99% pure) may be obtained from Avanti Polar Lipids Co. of Birmingham, Ala., Sigma Chemical Co. of St. Louis, Mo.

DPPC and CP are mixed in a weight ratio of 200:1 and combined with only the fluorocarbon propellants as in Example I. Then 5 mg of the mixture are aerosolized into a container, the chlorofluorocarbon propellants allowed to evaporate and the DPPC:CP crystals remaining are dissolved in 13 mg of propylene glycol. To this 20ml of distilled water are then added. The final mixture is heated to 50° C. and gently sonicated for 30 minutes. The artificial tears are then packaged in 15 ml drop dispensers.

The suspension is homogeneous. After standing for about 15 minutes at room temperature the suspension settles out on top of the aqueous phase but is easily resuspended by gentle shaking. The purity of the components was retained for at least seven months after manufacture.

Example III

Chromatagraphically pure DPPC and CP (99% pure) were obtained from Avanti Polar Lipids and the other companies previously listed.

DPPC and CP are mixed in a weight ratio of 200:1. To 5 mg of this mixture are added 100 mg of the drug Pilocarpine-HCl for delivery. This final mixture will ultimately result in a 1% solution of the drug when water is added. Pilocarpine-HCl can be purchased as IsotoCarpine-HCl from Alcon Pharmaceuticals. Next, the fluorocarbon propellants are added to the mixture as outlined in Example I. The mixture is atomized and the fluorocarbon propellants are allowed to evaporate. The 105 mg of the resulting mixture of DPPC:CP:Pilocarpine-HCl are dissolved in 50 mg of propylene glycol to which is added 20 ml of distilled water. The final mixture is heated to 45° C. and gently sonicated for 30 minutes. The drug delivery system for the eyes is then packaged in 15 ml drop dispensers.

The suspension is homogeneous. After standing for about 15 minutes at room temperature the suspension settles out on top of the aqueous phase but is easily resuspended by gentle shaking. The purity of the components was retained for at least seven months after manufacture.

Administration of Aerosol Drug Delivery System

The administration of the preparation as an aerosolized drug delivery system, prepared as described in EXAMPLE I above, delivers any drug or therapeutic agent by inhalation of the aerosol directly into the lungs, to the dermal, opthalmic, and mucous membranes and tissues such as but not limited to the hair, skin, nose, mouth, rectum, vagina, urethra, and throat.

Aerosol Characteristics

The diameter of aerosol particles was determined in a cascade impactor. Flow through the impactor was the same as aerosol flow from the nebulizer, 200 microliters/second. About 95% of the particles were equal to or less than 4 micron; the diameter of half of these was 1 micron. Mean particle diameter was 1.75±0.25 micron.

Structural characteristics after deposition were assessed by capturing the aerosolized particles on standard scanning electron microscopic grids fixed to glass slides, 22° C., dry. The lipids deposited on glass both as dry particles and as coalesced droplets. The latter evaporated immediately leaving dry lipid. The dry lipids were fixed in osmium vapor ($OsO_4$), coated and viewed with a scanning electron microscope. Crystalline figures, about 100 angstrums thick, were grouped in clumps on the dry surface. This is a unique configuration.

Impaction of the aerosolized crystalline figures on a liquid surface (normal saline solution, NSS) at 37° C., 100% humidity, in a surface balance resulted in a rapid spreading of a principally amorphous film that covered the entire surface (18.1 cm$^2$). Surface tension of the film was measured during expansion and compression at 37° C., 100% humidity. Film expansion to 110.4 cm$^2$ produced a surface tension of 72 dynes/cm and compression to 18.1 cm$^2$ lowered surface tension to less than 1 dyne/cm.

Delivery Of Aerosol To The Lungs

Initially the nozzle of the inhalation adapter was fitted directly to a 3.5 French Portex endotracheal tube (ETT), so that the aerosol traversed the length of the ETT before reaching the airways. It was found that greater than 85% of the aerosol lipids deposited on the ETT and, therefore the apparatus was modified as follows:

A 15 cm polyethylene extension tube (2 mm o.d., 0.5 mm i.d.) was bonded to the nozzle of the inhalation adapter for insertion through an ETT. Metered doses of aerosol delivered from the extension tube contained 5 mg DPPC per actuation with no deposition on the ETT. This is the delivery system used in the study on isolated, entubated rabbit lungs. The aerosol drug delivery system can be used with or without the extension nozzle depending upon the condition of the subject, i.e., whether or not the subject can effectively inhale without assistance.

To test delivery into the lungs, anesthetized (phenobarbtol, 30 mg/kg) adult rabbits were sacrificed by exsanguination and the lungs removed. An ETT was inserted to 1 cm above the carina. The extension tube from the aerosol generator was passed to <0.5 cm beyond the ETT. For these studies $^{14}$C-DPPC was added to the usual suspension. With the lung at resting volume, five actuations from the aerosol generator were delivered at 1 minute intervals. Tracheal pressure increased by less than 4 cm $H_2O$ during each actuation. The ETT was removed and the lungs were lavaged with NSS five times. Pooled lavage fluid was analyzed for $^{14}$C activity in a scintillation counter. The ETT was also rinsed with NSS and analyzed the same way. It was found that 74.6±5.2% of the activity was recovered in the lung lavage fluid, 2.8±0.17% was recovered from the ETT, and 22.6±1.3% remained in the lung.

Intrapulmonary Distribution Of Aerosol

In order to determine intrapulmonary distribution, lungs were flash frozen and dissected after delivery of $^{14}$C-DPPC labeled aerosol. Each lobe was sectioned into pieces between 0.15 and 0 6 gm, dissolved in Protosol and counted for $^{14}$C activity. Distribution was as follows: right upper lobe 0.5%, right middle lobe 39.6%, right lower lobe 21%, left upper lobe 22%, left lower lobe 3.8%, and trachea plus major airways 32.9%. Distribution was further broken down to 71% central and 29% peripheral, not including the major airways. Histologic survey of the lungs showed no significant changes from control in aerosol treated lungs.

Effect Of Aerosol On Pulmonary Mechanics

Lungs were excised from normal rabbits as described previously. The trachea was cannulated with a Portex ETT to approximately 10 mm above the carina. After degassing in a partial vacuum, volume-pressure (V-P) diagrams were recorded during stepwise inflation-deflation of the lungs between atmospheric (PO) and 30 cm $H_2O$ distending pressure (P30). Each pressure step was 5 cm $H_2O$, with a 2 minute pause between pressure steps. Three cycles were recorded; the third being used for comparisons. There were no further interventions in the control group. Prior to the third cycle, the placebo group received 5 actuations from the aerosol generator containing fluorocarbon propellants without mixture. The same protocol was followed in the treatment group, except that the mixture was aerosolized into the lungs prior to the third cycle. Intratracheal pressure changed insignificantly (less than 1 cm $H_2O$) during each actuation. The V-P diagrams recorded from each group were essentially the same. Only the volume in the treatment group at PO, end deflation was higher than the other groups.

Artificial Tears And Drug Delivery System For The Eye

The administration of the composition as an artificial tear and a drug delivery system for the eyes (prepared as described in EXAMPLES II and III above) is intended to serve as a tear replacement in dry eye syndromes and as a delivery system, by drops, for any drug into the eyes.

Characteristics

The surface tension lowering characteristics of the artificial tears/drug delivery system for the eyes was tested on a surface balance. Maximum surface area of 110 $cm^2$ required addition of 18 drops of the composition to simulate the addition of 3 drops into an eye having a surface area of approximately 25 $cm^2$. The surface was allowed to equilibrate and was then compressed and expanded repeatedly at a rate of 20 sec./cycle. Minimum surface tension after the first cycle was 28 dynes/cm. A minimum surface tension of 0 dynes/cm was achieved after about 1 minute of cycling. When cycled at faster rates, which approximate a blink, minimum surface tension was between 5 and 10 dynes/cm.

The composition does not irritate mucus membranes in the mouth, nose or eyes and is non-toxic.

We claim:

1. A process for preparing lipid crystals in combination with a therapeutically active substance comprising (a) admixing dipalmitoylphosphatidyl choline, one of the group of phospholipids known as fully saturated acyl chain phosphatidylcholines, and cholesteryl palmitate, in powder form, with a therapeutically active substance and one or more fluorocarbon propellants, said lipids being insoluble in the propellants; and (b) evaporating the propellants.

2. A process for preparing lipid crystals in combination with a therapeutically active substance comprising (a) admixing dipalmitoylphosphatidyl choline and cholesteryl palmitate, in powder form, with a therapeutically active substance and one or more fluorocarbon propellants, said lipids being insoluble in the propellants; and (b) evaporating the propellants.

3. The process defined in claim 2 wherein, simultaneously with or after step (b), the product of the process is delivered to the point of use.

4. The process defined in claim 2 wherein the phospholipids are present in an amount of about 90 to about 99.5 percent based on the weight of the mixture.

5. The product of the process of claim 1.

* * * * *